(12) United States Patent
Matsugu et al.

(10) Patent No.: US 6,589,911 B2
(45) Date of Patent: Jul. 8, 2003

(54) WEEDING METHOD WITH SODIUM HYDROGEN CARBONATE

(75) Inventors: Yutaka Matsugu, Kanagawa-ken (JP); Koji Hasegawa, Ibaraki-ken (JP)

(73) Assignee: The Hiraoka Environmental Science Laboratory, Kanagawa-ken (JP)

( * ) Notice: Subject to any disclaimer, the term of this patent is extended or adjusted under 35 U.S.C. 154(b) by 18 days.

(21) Appl. No.: 10/058,833

(22) Filed: Jan. 30, 2002

(65) Prior Publication Data
US 2002/0193252 A1 Dec. 19, 2002

(30) Foreign Application Priority Data

Jan. 18, 2001 (JP) ........................................ 2002-010870
Jan. 30, 2001 (JP) ........................................ 2001-022491

(51) Int. Cl.$^7$ ............................ A01N 3/02; A01N 59/00

(52) U.S. Cl. ............................................. 504/116; 504/119
(58) Field of Search ................................. 504/119, 116

(56) References Cited

FOREIGN PATENT DOCUMENTS

JP          07002602     *   1/1995

\* cited by examiner

Primary Examiner—Alton N Pryor
(74) Attorney, Agent, or Firm—Browdy and Neimark, P.L.L.C.

(57) ABSTRACT

Sodium hydrogen carbonate powder and/or an aqueous dispersion or solution of sodium hydrogen carbonate is sprayed to weeds by gravity Drop or low-pressure spraying, or blasted to weeds together with compressed air at an ejection pressure (gauge pressure) of 1–10 kgf/cm$^2$, using a high-pressure dry-blasting apparatus.

19 Claims, No Drawings

WEEDING METHOD WITH SODIUM HYDROGEN CARBONATE

FIELD OF THE INVENTION

The present invention relates to a weeding method for killing weeds with their roots intact by spraying sodium hydrogen carbonate in the form of powder or aqueous dispersion or solution, thereby dwarfing weeds of the next generation, particularly to a method for removing weeds in riverbanks, roads, railroads, airports, parks, farms, golf courses, etc. without affecting the environment.

PRIOR ART

Paying attention to influence on the environment, the use of herbicides is declining at present, so that weeding is carried out manually with cutting machines. However, weeding with cutting machines is highly costly in riverbanks, roads, railroads, airports, glass fields of parks, farms, golf courses, etc. having large areas. For instance, in an airport as large as the Haneda Airport, weeding costs 100,000,000 yen or more a year. Accordingly, a method for removing weeds at low cost without contaminating the environment is desired.

Known as other weeding methods using no herbicides than those using cutting machines are weeding methods comprising spraying seawater or sand, etc. However, the method of spraying seawater in place of herbicides is disadvantageous in causing damage by salt, etc. In addition, because the weeding method by spraying sand leads to the accumulation of sprayed sand after weeding, this method cannot be repeated.

Because the scattering of soil dust, etc. should be avoided in airports, it is desired that weeds remain as high as about 10 cm without being completely removed. For this purpose, weeding is carried out with cutting machines so that there remain weeds with some height, though much cost is needed for cutting operation in a wide area and treating the cut weeds.

The use of cutting machines is extremely dangerous in weeding operations on the slopes of roads, and the cutting machines cannot be used in railroads because they sputter stones. Further, because weeds on the slopes of these roads and railroads fiction to reinforce the ground and let rain water to flow downward without penetrating into the ground, they should not be killed completely. Thus, weeds on the slopes are preferably dwarfed.

OBJECT OF THE INVENTION

Accordingly, an object of the present invention is to provide a method for weeding efficiency without contaminating the environment, particularly to a method for dwarfing weeds of the next generation with their roots intact.

SUMMARY OF THE INVENTION

As a result of research in view of the above object, the inventors have found that by spraying sodium hydrogen carbonate powder and/or an aqueous dispersion or solution of sodium hydrogen carbonate to weeds, the weeds can be killed at a low cost without adversely affecting the environment, and the weeds of the next generation can be dwarfed. The present invention has been completed based on this finding.

Thus, the wedging method of the present invention comprises spraying sodium hydrogen carbonate powder and/or an aqueous dispersion or solution of sodium hydrogen carbonate to weeds.

Because sodium hydrogen carbonate is not only inexpensive but also soluble in water, and because a saturated aqueous solution of sodium hydrogen carbonate is nearly neutral at pH of about 8.2, it does not affect soil. In addition, the sodium hydrogen carbonate completely flows away with rainwater after weeding. With such low-cost sodium hydrogen carbonate not harmful to human beings and animals, weeds are removed with their roots in the soil intact. Though the treated weeds grow again, they tend to be lower in height than those untreated because of the function of sodium hydrogen carbonate, thereby reducing the number of weeding operations. The weeding method of the present invention using sodium hydrogen carbonate is classified to a low-pressure method and a high-pressure method, each being carried out by a dry or wet method as described below.

The first weeding method of the present invention comprises spraying sodium hydrogen carbonate powder and/or an aqueous dispersion or solution of sodium hydrogen carbonate to weeds by gravity drop or a low-pressure spraying apparatus. The aqueous dispersion or solution of sodium hydrogen carbonate preferably has a concentration of 5–15 weight %. The sodium hydrogen carbonate powder preferably has an average particle size of 10–500 $\mu$m.

The second weeding method of the present invention comprises blasting sodium hydrogen carbonate powder to weeds together with compressed air at an ejection pressure (gauge pressure) of 1–10 $kgf/cm^2$, using a high-pressure dry-blasting apparatus. The sodium hydrogen carbonate powder preferably has an average particle size of 10–500 $\mu$m.

The third weeding method of the present invention comprises is preparing an aqueous dispersion or solution of sodium hydrogen carbonate in advance, and blasting it to weeds at an ejection pressure (gauge pressure) of 100–2,500 $kgf/cm^2$ through a blasting nozzle of a high-pressure wet-blasting apparatus. The aqueous dispersion or solution of sodium hydrogen carbonate preferably has a concentration of 5–15 weight %.

The fourth weeding method of the present invention comprises using a high-pressure wet-blasting apparatus equipped with a high-pressure pump and a blasting nozzle; conveying water by the high-pressure pump to the blasting nozzle; adding sodium hydrogen carbonate powder to the incoming high-pressure water at the blasting nozzle; and blasting the resultant mixture to weeds at an ejection pressure (gauge pressure) of 100–2,500 $kgf/cf^2$. 100–500 g of sodium hydrogen carbonate powder is added per one litter of water. The sodium hydrogen carbonate powder preferably has an average particle size of 200 $\mu$m or more.

The first weeding method of the present invention comprises blasting an aqueous dispersion or solution of sodium hydrogen carbonate heated at 50–150° C. to weeds at an ejection pressure (gauge pressure) of 50–500 $kgf/cm^2$ through a blasting nozzle of a high-pressure wet-blasting apparatus. The aqueous dispersion or solution of sodium hydrogen carbonate has a concentration of preferably 50–150 g/L, more preferably 100–150 g/L.

The sixth weeding method of the present invention comprises using a high-pressure wet-blasting apparatus equipped with a high-pressure pump and a blasting nozzle; conveying heated water at 50–150° C. to said blasting nozzle by said high-pressure pump; adding sodium hydrogen carbonate powder to the incoming high-pressure, heated water at said blasting nozzle; and blasting the resultant mixture to weeds at an ejection pressure (gauge pressure) of 50–500 kgf/cm². 100–500 g of sodium hydrogen carbonate powder is preferably added per one litter of heated water. The sodium hydrogen carbonate powder preferably has an average particle size of 200 μm or more.

In any of the above methods, the amount of sodium hydrogen carbonate powder and/or an aqueous dispersion or solution of sodium hydrogen carbonate is preferably 0.00001–3.5 kg/m² by dry weight per a unit area of a field having weeds, though it may vary depending on the method. The sodium hydrogen carbonate powder and/or the aqueous dispersion or solution of sodium hydrogen carbonate is sprayed to weeds, preferably after cutting high weeds.

DESCRIPTION OF THE PREFERRED EMBODIMENTS

The weeding method of the present invention includes both of a method for spraying sodium hydrogen carbonate powder and/or an aqueous dispersion or solution of sodium hydrogen carbonate to weeds by gravity drop or by a low-pressure spraying apparatus, and a method using a high-pressure blasting apparatus.

[A] Sodium Hydrogen Carbonate Powder

The sodium hydrogen carbonate, which may be called sodium bicarbonate, used in the present invention is not limited to pure sodium hydrogen carbonate, but includes those containing impurities having no adverse influence on the environment. The sodium hydrogen carbonate powder is commercially available, and the commercially available products (trade name, "ARMEX", Church & Dwight Co., Inc.) shown in Table 1, for instance, may be used.

TABLE 1

| Grade No. | Particle Size Distribution |
|---|---|
| Composite Formula (100 μm grade) | Remaining on 140-mesh sieve (106 μm): ≧7% <br> Remaining on 200-mesh sieve (75 μm): ≧45% <br> Remaining on 325-mesh sieve (45 μm): ≦80% <br> Remaining on 400-mesh sieve (38 μm): ≦90% |
| Flow Formula M (200 μm grade) | Remaining on 60-mesh sieve (250 μm): ≦8% <br> Remaining on 100-mesh sieve (150 μm): ≧55% <br> Remaining on 170-mesh sieve (90 μm): ≧93% |
| Flow Formula XL (300 μm grade) | Remaining on 40-mesh sieve (425 μm): ≦8% <br> Remaining on 60-mesh sieve (250 μm): ≧60% <br> Remaining on 100-mesh sieve (150 μm): ≧70% <br> Remaining on 200-mesh sieve (75 μm): ≧80% <br> Remaining on 325-mesh sieve (45 μm): ≧90% |
| Maintenance Formula M (200 μm grade) | Remaining on 60-mesh sieve (250 μm): ≦8% <br> Remaining on 100-mesh sieve (150 μm): ≧55% <br> Remaining on 170-mesh sieve (90 μm): ≧93% |
| Maintenance Formula XL (300 μm grade) | Remaining on 40-mesh sieve (425 μm): ≦8% <br> Remaining on 60-mesh sieve (250 μm): ≧60% <br> Remaining on 100-mesh sieve (150 μm): ≧70% <br> Remaining on 200-mesh sieve (75 μm): ≧80% <br> Remaining on 325-mesh sieve (45 μm): ≧90% |
| Profile Formula XL (300 μm grade, containing about 10% of sand of 300 μm in particle size) | Remaining on 40-mesh sieve (425 μm): ≦8% <br> Remaining on 60-mesh sieve (250 μm): ≧55% <br> Remaining on 100-mesh sieve (150 μm): ≧70% <br> Remaining on 200-mesh sieve (75 μm): ≧80% <br> Remaining on 325-mesh sieve (45 μm): ≧90% |

[B] Weeding Method
[1] Weeding Method by Gravity Drop or Low-Pressure Spraying

The spraying of sodium hydrogen carbonate powder and/or an aqueous dispersion or solution of sodium hydrogen carbonate by gravity drop or by using a low-pressure spraying apparatus means that the sodium hydrogen carbonate powder and/or the aqueous dispersion or solution of sodium hydrogen carbonate is sprayed to weeds without pressure or with low pressure, regardless of whether or not the spraying apparatus is used. For instance, (a) a method of causing sodium hydrogen carbonate powder or an aqueous dispersion solution of sodium hydrogen carbonate to flow through a small pore of a bottom wall of a container, (b) a method of spraying sodium hydrogen carbonate powder, etc. by manually swinging a nozzle-equipped hose of a shoulder-back or self-movable spraying apparatus, (c) a method of manually or automatically spraying sodium hydrogen carbonate powder, etc. through a nozzle-equipped hose of a spraying apparatus mounted onto a vehicle, etc. may be listed.

The weeding operation of spring or summer weeds and autumn or summer weeds by gravity drop or low-pressure spraying is carried out preferably when weeds are as high as about 30 cm or less, more preferably when they are as high as about 10–20 cm or less. When the weeds are treated at a height of about 10–20 cm or less, only a small amount of sodium hydrogen carbonate needs to be sprayed.

When sodium hydrogen carbonate powder is sprayed, it has an average particle size of preferably 10–500 μm, more preferably 10–300 μm When the sodium hydrogen carbonate powder has an average particle size of less than 10 μm, it is too light in weight, resulting in too high a percentage thereof scattered before impinging on weeds. On the other hand, when the sodium hydrogen carbonate powder has an average particle size of more than 500 μm the percentage of sodium hydrogen carbonate powder repulsed by weeds is too large, resulting in small weeding effect. Incidentally, the larger average particle size the sodium hydrogen carbonate powder has, the larger weeding effect is obtained by the same amount of sodium hydrogen carbonate powder sprayed.

To reduce the percentage of sodium hydrogen carbonate powder scattering before or after impinging on weeds, the sodium hydrogen carbonate powder preferably has as narrow a particle size distribution as possible. Incidentally, water is preferably sprayed slightly to leaves and stems of weeds before spraying the sodium hydrogen carbonate powder, because it makes it easy for the sodium hydrogen carbonate powder to attach to weeds.

In the case of an aqueous dispersion or solution of sodium hydrogen carbonate, its concentration is preferably 5–15 weight %. When its concentration is less than 5 weight %, a large amount of the aqueous dispersion or solution should be sprayed at a time, and/or it should be sprayed many times, resulting in low efficiency in the weeding operation. On the other hand, even if the concentration of the aqueous dispersion or solution of sodium hydrogen carbonate exceeds 15 weight %, the correspondingly improved efficiency in the weeding operation cannot be achieved. When a high-concentration aqueous solution of sodium hydrogen carbonate should be sprayed, the aqueous solution of sodium hydrogen carbonate needs only to be heated. When an aqueous dispersion of sodium hydrogen carbonate is used, the aqueous is preferably stirred such that the dispersion of sodium hydrogen carbonate is kept uniform.

[2] Blast-weeding Method
(1) Powder Blasting Method

The blasting method with sodium hydrogen carbonate powder uses a high-pressure dry-blasting apparatus having a blasting nozzle, through which the sodium hydrogen carbonate powder is ejected to weeds together with a compressed air at an ejection pressure (gauge pressure) of 1–10 kgf/cm², thereby carrying out weeding. Because the sodium hydrogen carbonate powder impinges on the leaves and stems of weeds to damage their issues, the weeds can effectively be killed in cooperation with the function of sodium hydrogen carbonate to open the stoma of leaves. The powder blasting method can kill weeds with their leaves turned yellow or black the day after blasting.

The sodium hydrogen carbonate powder used in the powder blasting method should have a particle size at which it can be ejected through a blasting nozzle at a proper speed, and such hardness that can damage the leaves and stems of weeds.

The average particle size of sodium hydrogen carbonate powder affecting the ejection speed of sodium hydrogen carbonate powder is preferably 10–500 $\mu$m. When the sodium hydrogen carbonate powder has an average particle size of less than 10 $\mu$m, it is too light in weight, failing to impinge on weeds at a sufficient speed even if the sodium hydrogen carbonate powder is ejected with a compressed air, and thus resulting in scattering at a high percentage before impinging on weeds. On the other hand, even if the sodium hydrogen carbonate powder has an average particle size of more than 500 $\mu$m the result is only that a large amount of sodium hydrogen carbonate powder is used, failing to obtain the correspondingly improved effect of damaging weeds. Thus, it is economically meaningless. The average particle size of sodium hydrogen carbonate powder is particularly preferably 100–300 $\mu$m Incidentally, to make the energy of sodium hydrogen carbonate powder impinging on weeds uniform it is preferable to use sodium hydrogen carbonate powder having a narrow particle size distribution.

The particle size of the sodium hydrogen carbonate powder is preferably determined depending on the types of weeds. For instance, the sodium hydrogen carbonate powder having a particle size of 100 $\mu$m or less is suitable for removing weeds with soft leaves and low weeds. Particularly when low weeds are to be killed, it is preferable to blast sodium hydrogen carbonate powder having a particle size of 100 $\mu$m or less at relatively low pressure, because too high blasting pressure blows away the soil. Further, the sodium hydrogen carbonate powder having a particle size of 100–200 $\mu$m functions to damage the leaves and stems of weeds, in addition to the effect inherent in sodium hydrogen carbonate to kill weeds by opening the stoma of their leaves, whereby it be used for blast weeding effective for as low weeds as up to about 40 cm The sodium hydrogen carbonate powder having a particle size of 200–300 $\mu$m is suitable for from low weeds to high weeds of about 60 cm.

The sodium hydrogen carbonate powder is preferably granular, such that it has enough hardness to damage the leaves and stems of weeds. The granules are relatively large particles formed by aggregating fine powder of sodium hydrogen carbonate, which can be partially broken when impinging on weeds. The granular particles of sodium hydrogen carbonate preferably have hardness, as Mohs hardness, of about 2.0 or more. When the Mohs hardness of the granular particles is less than 2.0, the granular particles are destroyed at the time of impingement, they do not have large effect of damaging the leaves and stems of weeds. Particularly preferably the sodium hydrogen carbonate powder has Mohs hardness of 2.5 or more.

To enhance the weeding effect, sand may be added to the sodium hydrogen carbonate powder. The sand preferably has an average particle size of 100–500 $\mu$m. The percentage of the sand added is 30 parts by weight or less, preferably 15 parts by weight or less per 100 parts by weight of the sodium hydrogen carbonate powder. Particularly when as high weeds as 60 cm or more having relatively thick stems are to be removed, sand may effectively be added to sodium hydrogen carbonate powder.

The blasting pressure (pressure of ejection from nozzle, gauge pressure) of compressed air used in the powder blasting method is preferably 1–10 $kgf/cm^2$, particularly preferably 3–6 $kgf/cm^2$. The flow rate of air used in the powder blasting method, which may be determined depending on the size of a blasting nozzle, is generally 0.5–20 $m^3$/minute, particularly preferably 1–15 $m^3$/minute. The amount sodium hydrogen carbonate powder ejected is preferably 0.1–5 kg/minute, particularly preferably 0.5–2.3 kg/minute. The ejection time, which may vary depending on the blasting conditions, is preferably 20–180 second/$m^2$.

The powder blasting method is classified to a wet powder blasting method in which water is sprayed in the form of mist during the blasting operation to prevent the scattering of sodium hydrogen carbonate powder and to make it easy for the sodium hydrogen carbonate powder to attach to weeds, and a dry powder blasting method in which water is not used at all. In the case of the wet method, it is preferable that a water-spraying nozzle is mounted near a tip end of a blasting nozzle to spray water in the form of curtain. The amount of water sprayed is preferably 0.1–5 litter/minute, more preferably 1–2 litter/minute.

(2) Liquid Blasting Method (a) Normal-temperature, High-pressure Water Blasting Method The normal-temperature, high-pressure water blasting method is a method for removing weeds by damaging, cutting and tearing their leaves and stems, utilizing the destroying power of water such as impingement power, pulsating pressure, wedging effect, cavitation phenomenon, etc. The weeds treated by the normal-temperature, high-pressure water blasting method are killed with their leaves turned yellow or black the next day of blasting. In addition, because sodium hydrogen carbonate has a function to dwarf weeds of the next generation, the blasting of an aqueous dispersion or solution of sodium hydrogen carbonate to weeds 3–5 times a year can keep the weeds low.

The normal-temperature, high-pressure water blasting method is classified to (i) a method comprising preparing an aqueous dispersion or solution of sodium hydrogen carbonate in advance, and ejecting it through a blasting nozzle of a high-pressure wet-blasting apparatus, and (ii) a method comprising conveying water to a blasting nozzle by a high-pressure pump, adding sodium hydrogen carbonate powder to the incoming high-pressure water at the blasting nozzle, and ejecting a mixture of sodium hydrogen carbonate powder and water through the blasting nozzle Method (i)

The aqueous dispersion or solution of sodium hydrogen carbonate prepared in advance has a concentration of preferably 5–15 weight %, more preferably 6–9 weight %, particularly preferably 7–8.5 weight %. When the concentration is less than 5 weight %, sufficient function to dwarf weeds cannot be obtained. On the other hand, even if it exceeds 15 weight %, the correspondingly improved effect cannot be obtained.

By blasting the aqueous dispersion or solution having the above concentration to weeds at an ejection pressure (gauge pressure) of 100–2,500 $kgf/cm^2$, the leaves and stems of weeds can be damaged, cut and tom. When the ejection pressure is less than 100 $kgf/cm^2$, there is only too small weeding effect. On the other hand, when it is more than 2500 $kgf/cm^2$, too much load is applied to the blasting apparatus. The particularly preferred ejection pressure (gauge pressure) of the aqueous dispersion or solution is 200–1,500 $kgf/cm^2$. Incidentally, because the aqueous dispersion or solution ejected through the nozzle has extremely decreased pressure when impinging on weeds, it does not damage the soil ground per se.

The amount of the aqueous dispersion or solution of sodium hydrogen carbonate ejected is preferably 5–1000 litter/minute, more preferably 15–500 litter/minute. Though changeable depending on the ejecting conditions, the ejection time is preferably 5–20 second/m².

To enhance the weeding efficiency, it is possible to use a rotary nozzle as the blasting nozzle. The rotary nozzle includes, for instance, a rotary nozzle having two orifices, and an eccentric rotary nozzle having a large number of small-diameter nozzle tips.

Method (ii)

This method is a method comprising using a high-pressure wet-blasting apparatus equipped with a high-pressure pump and a blasting nozzle; conveying water to the blasting nozzle by the high-pressure pump; adding sodium hydrogen carbonate powder to the incoming high-pressure water at the blasting nozzle; and ejecting the resultant mixture through the blasting nozzle. Because conditions such as the pressure and amount of a mixture of sodium hydrogen carbonate powder and water, etc. may be the same as in the above method (i), their explanation will be omitted here.

Though the sodium hydrogen carbonate powder added at the blasting nozzle is not restrictive, the granular sodium hydrogen carbonate powder is particularly preferable. Particularly when the sodium hydrogen carbonate powder having an average particle size of 200 $\mu$m or more is used, the sodium hydrogen carbonate powder added at the blasting nozzle is not completely dissolved in water, so that it partially impinges on weeds in the form of a solid with high weeding efficiency.

The amount of sodium hydrogen carbonate powder added is preferably 100–500 g per one litter of water. When the amount of sodium hydrogen carbonate powder added is less than 100 g/L, sufficient effects of removing weeds and dwarfing the next generation weeds cannot be obtained. On the other hand, when it is more than 500 g/l, the soil becomes too alkaline, thereby being likely to kill the roots of weeds. The more preferred amount of sodium hydrogen carbonate powder added is 200–300 g per one litter of water.

(b) Steam Blasting Method

The steam blasting method is a method for removing weeds by damaging, cutting and tearing their leaves and stems, utilizing the destroying power of heated water such as impingement power, pulsating pressure, wedging effect, cavitation phenomenon, etc., in addition to the weeding function of sodium hydrogen carbonate per se. Because the concentration of an aqueous dispersion or solution of sodium hydrogen carbonate can be increased by elevating the temperature of the aqueous dispersion or solution to 50–150° C., a larger effect of killing weeds can be obtained than the normal-temperature, high-pressure water blasting method. The weeds subjected to the steam blasting method are killed with their leaves turned yellow or black the next day of treatment.

The steam blasting method is classified to (i) a method comprising preparing an aqueous dispersion or solution of sodium hydrogen carbonate heated at 50–150° C., and ejecting it; and (ii) a method comprising conveying heated water at 50–150° C. to a blasting nozzle by a high-pressure pump, adding sodium hydrogen carbonate powder to the incoming heated high-pressure water at the blasting nozzle, and ejecting the resultant mixture through the blasting nozzle. The blasting nozzle may be the same as described above.

Method (i)

The temperature of an aqueous dispersion or solution of sodium hydrogen carbonate is preferably 50–150° C. Heating at 50–150° C. increases the effect of damaging the leaves and stems of weeds. It also increases the solubility of sodium hydrogen carbonate in water, so that an aqueous solution of sodium hydrogen carbonate has a higher concentration, resulting in the improvement of a function to dwarf weeds. The temperature of the aqueous dispersion or solution is particularly preferably 65° C. or higher.

The concentration of an aqueous dispersion or solution of sodium hydrogen carbonate is preferably 50–150 g/L, more preferably 100–150 g/L. When the concentration of the aqueous dispersion or solution is less than 50 g/L, sufficient function to dwarf weeds cannot be obtained. On the other hand, even if it exceeds 150 g/L, the correspondingly improved function of weeding cannot be obtained.

The aqueous dispersion or solution of sodium hydrogen carbonate having the above concentration at 50–150° C. is blasted to weeds at an ejection pressure (gauge pressure) of 50–500 kgf/cm². When the ejection pressure of the aqueous dispersion or solution of sodium hydrogen carbonate is less than 50 kgf/cm², a sufficient effect of damaging the leaves and stems of weeds cannot be obtained. On the other hand, even if it is more than 500 kgf/cm², the correspondingly improved weeding function cannot be obtained. The ejection pressure is preferably 100–300 kgf/cm², particularly preferably 150–300 kgf/cm².

The amount of an aqueous dispersion or solution of sodium hydrogen carbonate ejected is preferably 10–100 litter/minute, more preferably 30–70 litter/minute. Though changeable depending on the blasting conditions, the ejection time of an aqueous dispersion or solution of sodium hydrogen carbonate is preferably 5–20 second/m².

Method (ii)

This method is the same as the normal-temperature, high-pressure water blasting method using water at normal temperature, except for using water heated at 50–150° C. as pressured water and setting the ejection pressure (gauge pressure) at 50–500 kgf/cm². The effect of pressurized water and the significance of the ejection pressure are the same as described above.

Incidentally, a combination of various blasting methods provides more improved weeding effect. For instance, after killing and dwarfing weeds to some extent by the powder blasting method, the normal-temperature, high-pressure water blasting method and the steam blasting method may be carried out several times a year to keep the dwarfing of weeds.

[C] Amount of Spraying

In both cases of the weeding method by gravity drop or low-pressure spraying and the blasting weeding method, the amount of sodium hydrogen carbonate powder and/or an aqueous dispersion or solution of sodium hydrogen carbonate sprayed in a single operation is preferably 0.00001–3.5 kg/m² by dry weight of sodium hydrogen carbonate.

Particularly in the case of the weeding method by gravity drop or low-pressure spraying, spraying is carried out in an amount of preferably 0.00001–1 kg/m², particularly preferably 0.1–0.5 kg/m², by dry weight of sodium hydrogen carbonate. In the case of the blasting weeding method, the spraying amount is preferably 0.2–3.5 kg/m². Sodium hydrogen carbonate in an amount in this range provides proper weeding effect.

Though the frequency of spraying sodium hydrogen carbonate may vary depending on the amount of sodium hydrogen carbonate sprayed in a single operation, the types of weeds, and climate conditions such as temperature, sunshine, humidity, etc., it is preferably once per 1–2 months in the summer, and once per about 2–4 months in other seasons. Because the dwarfing of weeds is stable after 2 years from spraying, the spraying of sodium hydrogen carbonate may be enough at a frequency of about 2–3 times a year.

With sodium hydrogen carbonate sprayed, the weeds are killed with their leaves turned yellow or black. For instance, in the case of Equisetaceae weeds, Leguminosae weeds and wide leaves weeds, they start to die in 1–2 days in summer and 4–5 days in autumn after spraying. Gramineae weeds except for grass (Zoysia japonica) start to die by conducting the spraying of sodium hydrogen carbonate once a week for 2–3 weeks.

[D] Removable Weeds

The weeds that can be removed by the method of the present invention include, for instance, wide leaves weeds such as Taraxacum, *Chenopodium album, Amaranthus retroflexus, Amaranthus lividus, Portulaca oleracea, Stellaria media, Rumex japonicus, Polygonum longisetum, Capsella bursa-pastoris, Cassia tora*, etc., Equisetaceae weeds such as *Equisetum arvense*, etc., Gramineae weeds such as *Imperata cylindrica*, Japanese nutmeg, *Coix lacryma-jobi, Echinochloa crus-galli, Setaria viridis, Digitaria adscendens, Eleusine indica*, Japanese pampas grass, etc., Cyperaceae weeds such as *Cyperus rotundus, Cyperus microiria, Cyperus glomeratus*, etc.

The present invention will be described in detail referring to EXAMPLES below without intention of limiting the present invention thereto.

EXAMPLE 1

A mixture of *Equisetum arvense* and Taraxacum having an average height of about 20 cm and grass having an average height of about 10 cm in a test field having an area of 0.5 $m^2$ in Yokohama-city, Konagawn-prefecture, Japan were subjected to the following field weeding test in the last third of October. In this EXAMPLE, commercially available sodium hydrogen carbonate powder (Composite Formula having a particle size of 100 $\mu$m, available from Church & Dwight Co., Inc.) was charged into a container of 200 $cm^3$ in volume having a bottom wall provided with a small pore of 1 mm in diameter, and the sodium hydrogen carbonate powder was sprayed by gravity drop through the small pore.

First, after water is sprayed to a mixture of *Equisetum arvense* and Taraxacum and grass, sodium hydrogen carbonate powder was uniformly sprayed in an amount of 10 mg/$m^2$, 20 mg/$m^2$, 30 mg/$m^2$ and 40 mg/$m^2$, respectively. From 2–3 days after spraying, part of *Equisetum arvense* and Taraxacum started to die with their leaves tuned black, and part of grass started to die with their leaves turned yellow. The killing degree of the weeds was measured by the naked eye after 9 days from spraying to determine the killing rate of weeds, assuming that the killing rate was 100% when all of *Equisetum arvense* and Taraxacum and all of grass were respectively killed. The results are shown in Table 2.

TABLE 2

| Amount of Sodium Hydrogen Carbonate Powder Sprayed (mg/$m^2$) | | 10 | 20 | 30 | 40 |
|---|---|---|---|---|---|
| Killing Rate of Weeds (%) | Equisetum Arvenseand | 10 | 30 | 55 | 65 |

TABLE 2-continued

| Amount of Sodium Hydrogen Carbonate Powder Sprayed (mg/$m^2$) | 10 | 20 | 30 | 40 |
|---|---|---|---|---|
| Taraxacum | | | | |
| Grass | 15 | 45 | 60 | 75 |

As shown in Table 2, the killing rate of weeds increased as the amount of sodium hydrogen carbonate powder sprayed increased, and the weeding effect was remarkable particularly when the amount of sodium hydrogen carbonate powder sprayed was 30 mg/$m^2$ or more.

EXAMPLE 2

A mixture of *Equisetum arvense* and Taraxacum having an average height of about 20 cm and grass having an average height of about 10 cm in a test field having an area of 0.5 $m^2$ in Yokohama-city, Kanagawa-prefecture, Japan were subjected to a field weeding test by spraying an aqueous solution of sodium hydrogen carbonate with a watering pot in the last third of October.

An aqueous solution of sodium hydrogen carbonate having a concentration of 2.5 weight %, 5.0 weight %, 8.0 weight % and 10.0 weight %, respectively, was uniformly sprayed to a mixture of *Equisetum arvense* and Taraxacum and grass in an amount of 400 mL/$m^2$ for each. From 2–3 days after spraying, part of *Equisetum arvense* and Taraxacum started to die with their leaves turned black, and part of grass started to die with their leaves turned yellow. The killing degree of the weeds was measured by the naked eye after 9 days from spraying to determine the killing rate of weeds in the same manner as in EXAMPLE 1. The results are shown in Table 3.

TABLE 3

| Concentration of Aqueous Solution of Sodium Hydrogen Carbonate (weight %) | | 2.5 | 5.0 | 8.0 | 10.0 |
|---|---|---|---|---|---|
| Killing Rate of Weeds (%) | Equisetum arvense and Taraxacum | 10 | 30 | 65 | 80 |
| | Grass | 40 | 50 | 70 | 85 |

As is clear from Table 3, the killing rate of weeds increased as the concentration of the aqueous solution of sodium hydrogen carbonate increased, and the weeding effect was remarkable particularly when the concentration was 8.0 weight % or more.

EXAMPLE 3

A mixture of *Equisetum arvense* and Taraxacum having an average height of about 5 cm and *Imperata cylindrica* having an average height of about 5 cm in a test field having an area of 0.5 $m^2$ in Yokohama-city, Kanagawa-prefecture, Japan were subjected to the following field weeding test from the last third of July to the first third of November. Area ratios at which the mixture of *Equisetum arvense* and Taraxacum and *Imperata cylindrica* covered the test field were as shown in Table 6. Incidentally, the area ratio of weeds was assumed as 100% when the weeds proliferated to such an extent that they completely concealed the soil surface.

A saturated aqueous solution of sodium hydrogen carbonate was sprayed to each test field in an amount of 400 ml/$m^2$ by a watering pot, and then sprayed in the same way after 7 days, 14 days and 21 days, respectively. The area ratio and average height of weeds were measured by the naked eye after 26 days from the start of spraying. The weeds were totally cut after 54 days from the start of spraying. Thereafter, the weeds were left to grow without spraying an aqueous solution of sodium hydrogen carbonate. The area ratio and average height of weeds were measured by the naked eye after 64 days, 67 days, 73 days, 78 days, 86 days, 91 days and 95 days, respectively, from the start of spraying. For comparison, a mixture of *Equisetum arvense* and Taraxacum and *Imperata cylindrica*, to which an aqueous solution of sodium hydrogen carbonate was not sprayed, were subjected to the same measurement with respect to an area ratio and an average height. The results are shown in Table 4.

TABLE 4

| | | Equisetum Arvense and Taraxacum | | | |
| | | Yes | | No | |
| Days Passed | Treatment | Area Ratio of Weeds (%) | Average Height (cm) | Area Ratio of Weeds (%) | Average Height (cm) |
| --- | --- | --- | --- | --- | --- |
| 0 | Spraying | 50 | 5 | 50 | 5 |
| 7 | Spraying | 5 | 0 | 70 | 5 |
| 14 | Spraying | 5 | 0 | 80 | 10 |
| 21 | Spraying | 5 | 0 | 90 | 20 |
| 26 | — | 5 | 0 | 100 | 20 |
| 54 | Cutting | 0 | 0 | 0 | 0 |
| 64 | — | 0 | 0 | 20 | 5 |
| 67 | — | 0 | 0 | 30 | 7 |
| 73 | — | 5 | 5 | 50 | 10 |
| 78 | — | 10 | 7 | 70 | 15 |
| 86 | — | 10 | 10 | 80 | 20 |
| 91 | — | 20 | 10 | 90 | 20 |
| 95 | — | 20 | 10 | 90 | 25 |

| | | Imperata Cylindrica | | | |
| | | Yes | | No | |
| Days Passed | Treatment | Area Ratio of Weeds (%) | Average Height (cm) | Area Ratio of Weeds (%) | Average Height (cm) |
| --- | --- | --- | --- | --- | --- |
| 0 | Spraying | 5 | 5 | 5 | 5 |
| 7 | Spraying | 10 | 15 | 30 | 25 |
| 14 | Spraying | 30 | 25 | 70 | 50 |
| 21 | Spraying | 50 | 45 | 80 | 70 |
| 26 | — | 50 | 50 | 90 | 80 |
| 54 | Cutting | 0 | 0 | 0 | 0 |
| 64 | — | 0 | 0 | 5 | 3 |
| 67 | — | 0 | 0 | 5 | 5 |
| 73 | — | 0 | 0 | 10 | 10 |
| 78 | — | 5 | 5 | 30 | 10 |
| 86 | — | 5 | 7 | 50 | 15 |
| 91 | — | 5 | 7 | 70 | 15 |
| 95 | — | 5 | 10 | 80 | 20 |

It is clear from Table 4 that by spraying an aqueous solution of sodium hydrogen carbonate, it is possible not only to remove weeds but also to suppress the sprouting of weeds of the next generation, thereby dwarfing them.

EXAMPLE 4

Sodium hydrogen carbonate powder ("Composite Formula" having a particle size 100 μm available from Church & Dwight Co., Inc.) was charged into a container of 200 cm$^3$ in volume having a bottom wall provided with a small pore of 1 mm in diameter. A field weeding test was carried out by spraying the sodium hydrogen carbonate powder through the small pore by gravity drop in the same manner as in EXAMPLE 3 except for setting the amount of spraying at 33 mg/m$^2$ per one operation. The results are shown in Table 5.

TABLE 5

| | | Equisetum Arvense and Taraxacum | | | |
| | | Yes | | No | |
| Days Passed | Treatment | Area Ratio of Weeds (%) | Average Height (cm) | Area Ratio of Weeds (%) | Average Height (cm) |
| --- | --- | --- | --- | --- | --- |
| 0 | Spraying | 50 | 5 | 50 | 5 |
| 7 | Spraying | 5 | 0 | 50 | 7 |
| 14 | Spraying | 10 | 0 | 70 | 10 |
| 21 | Spraying | 10 | 0 | 80 | 15 |
| 26 | — | 20 | 0 | 90 | 20 |
| 54 | Cutting | 0 | 0 | 0 | 0 |
| 64 | — | 5 | 7 | 10 | 5 |
| 67 | — | 5 | 7 | 20 | 10 |
| 73 | — | 10 | 7 | 40 | 10 |
| 78 | — | 20 | 10 | 60 | 18 |
| 86 | — | 30 | 10 | 80 | 18 |
| 91 | — | 50 | 10 | 90 | 20 |
| 95 | — | 60 | 10 | 90 | 25 |

| | | Imperata Cylindrica | | | |
| | | Yes | | No | |
| Days Passed | Treatment | Area Ratio of Weeds (%) | Average Height (cm) | Area Ratio of Weeds (%) | Average Height (cm) |
| --- | --- | --- | --- | --- | --- |
| 0 | Spraying | 0 | 5 | 0 | 5 |
| 7 | Spraying | 10 | 20 | 10 | 20 |
| 14 | Spraying | 50 | 25 | 70 | 50 |
| 21 | Spraying | 70 | 50 | 90 | 70 |
| 26 | — | 90 | 55 | 100 | 90 |
| 54 | Cutting | 0 | 0 | 0 | 0 |
| 64 | — | 0 | 0 | 0 | 0 |
| 67 | — | 0 | 0 | 5 | 5 |
| 73 | — | 5 | 5 | 10 | 10 |
| 78 | — | 10 | 10 | 20 | 15 |
| 86 | — | 20 | 13 | 40 | 15 |
| 91 | — | 20 | 13 | 50 | 20 |
| 95 | — | 30 | 13 | 70 | 20 |

As is clear from Table 5, the spraying of sodium hydrogen carbonate powder can not only remove weeds, but also suppress the sprouting of weeds of the next generation, thereby dwarfing them.

EXAMPLE 5

Weeds mainly consisting of grass, *Artemisia princeps* and *Equisetum arvense* having an average height of about 20 cm on a roadside in Yokohama-city, Kanagawa-prefecture, Japan were subjected to a field weeding test by a dry powder blasting method comprising ejecting sodium hydrogen carbonate powder through a blasting nozzle, under the conditions shown in Table 6 using a blasting apparatus ("Accustrip System 11 sx" available from Church & Dwight Co., Inc.) in July.

TABLE 6

| Conditions of Dry Powder Blasting Method | |
| --- | --- |
| Sodium Hydrogen Carbonate Powder | Composite Formula[1] |
| Amount of Compressed Air Ejected | 3.5 m$^3$/minute |
| Blasting Pressure (gauge pressure)[2] | 2 kgf/cm$^2$ |
| Amount of Sodium Hydrogen Carbonate | 0.35 kg/m$^2$ |

TABLE 6-continued

Conditions of Dry Powder Blasting Method

| | |
|---|---|
| Powder Ejected | |
| Ejection Time | 20 second/m$^2$ |
| Nozzle | #4 Fan Nozzle |

Note:
[1]Having a particle size of 100 μm, available from Church & Dwight Co., Inc.
[2]Pressure of ejection from nozzle.

These weeds were killed with the leaves of grass turned yellow and the leaves of *Artemisia princeps* and *Equisetum arvense* turned black the next day of treatment in an area where the above treatment was carried out.

EXAMPLE 6

Weeds mainly consisting of *Artemisia princeps*, Japanese nutmeg and *Solidago serotina* having an average height of about 40 cm on a roadside in Yokohama-city, Kanagawa-prefecture, Japan were subjected to a field weeding test by a wet powder blasting method comprising ejecting sodium hydrogen carbonate powder through a blasting nozzle and water spray through a water-spraying nozzle, under the conditions shown in Table 7 using a blasting apparatus ("Accustrip System 11 sx" available from Church & Dwight Co., Inc.) in July.

TABLE 7

Conditions of Wet Powder Blasting Method

| | |
|---|---|
| Sodium Hydrogen Carbonate Powder | Flow Formula M[1] |
| Amount of Compressed Air Ejected | 3.5 m$^3$/minute |
| Blasting Pressure (gauge pressure)[2] | 2.5 kgf/cm$^2$ |
| Amount of Sodium Hydrogen Carbonate Powder Ejected | 0.7 kg/m$^2$ |
| Ejection Time | 40 second/m$^2$ |
| Nozzle | #4 Fan Nozzle |

Note:
[1]Having a particle size of 200 μm, available from Church & Dwight Co., Inc.
[2]Pressure of ejection from nozzle.

These weeds were killed with the leaves of Japanese nutmeg turned yellow and the leaves of *Artemisia princeps* and *Solidago serotina* turned black the next day of treatment in an area where the above treatment was carried out.

EXAMPLE 7

Weeds mainly consisting of Japanese nutmeg, *Coix lacryma-jobi* and *Solidago serotina* having an average height of about 60 cm on a roadside in Yokohama-city, Kanagawa-prefecture, Japan were subjected to a field weeding test by a wet powder blasting method comprising ejecting sodium hydrogen carbonate powder through a blasting nozzle and water spray through a water-spraying nozzle, under the conditions shown in Table 8 using a blasting apparatus ("Accustrip System 11 sx" available from Church & Dwight Co., Inc.) in July.

TABLE 8

Conditions of Wet Powder Blasting Method

| | |
|---|---|
| Sodium Hydrogen Carbonate Powder | Flow Formula XL[1] |
| Amount of Compressed Air Ejected | 3.5 m$^3$/minute |
| Blasting Pressure (gauge pressure)[2] | 3.0 kgf/cm$^2$ |
| Amount of Sodium Hydrogen Carbonate Powder Ejected | 1.2 kg/m$^2$ |
| Ejection Time | 60 second/m$^2$ |
| Nozzle | #4 Fan Nozzle |

Note:
[1]Having a particle of size 300 μm, available from Church & Dwight Co., Inc.
[2]Pressure of ejection from nozzle.

These weeds were killed with the leaves of Japanese nutmeg and *Coix lacryma-jobi* turned yellow and the leaves of *Solidago serotina* turned black the next day of treatment in an area where the above treatment was carried out.

EXAMPLE 8

Weeds mainly consisting of *Coix lacryma-jobi*, *Pueraria lobata*, Japanese nutmeg and *Solidago serotina* having an average height of about 100 cm on a roadside in Yokohama-city, Kanagawa-prefecture, Japan were cut to an average height of about 60 cm in July. Soon after, they were subjected to a field weeding test by a wet powder blasting method comprising ejecting sodium hydrogen carbonate powder through a blasting nozzle and water spray through a water-spraying nozzle, under the conditions shown in Table 9 using a blasting apparatus ("Accustrip System 12sx" available from Church & Dwight Co., Inc.).

TABLE 9

Conditions of Wet Powder Blasting Method

| | |
|---|---|
| Sodium Hydrogen Carbonate Powder | Profile Formula XL[1] |
| Amount of Compressed Air Ejected | 11 m$^3$/minute |
| Blasting Pressure (gauge pressure)[2] | 3.0 kgf/cm$^2$ |
| Amount of Sodium Hydrogen Carbonate Powder Ejected | 0.6 kg/m$^2$ |
| Ejection Time | 30 second/m$^2$ |
| Nozzle | #6 Fan Nozzle |

Note:
[1]Having a particle size of 300 μm and containing 10% of sand, available from Church & Dwight Co., Inc.
[2]Pressure of ejection from nozzle.

These weeds were killed with the leaves of *Coix lacryma-jobi* and Japanese nutmeg turned yellow and the leaves of *Pueraria lobata* and *Solidago serotina* turned black the next day of treatment in an area where the above treatment was carried out.

EXAMPLE 9

Weeds mainly consisting of Japanese nutmeg, *Coix lacryma-jobi*, *Pueraria lobata* and *Solidago serotina* having an average height of about 60 cm on a roadside in Yokohama-city, Kanagawa-prefecture, Japan were subjected to a field weeding test by a normal-temperature, high-pressure water blasting method under the conditions shown in Table 10 using a blasting apparatus ("Jetman FCPS-1030", available from Zaoh Sangyo K. K.) in July.

TABLE 10

Conditions of Normal-Temperature, High-Pressure Water Blasting Method

| | |
|---|---|
| Concentration of Aqueous Solution of Sodium Hydrogen Carbonate | 70 g/L |
| Blasting Pressure (gauge pressure) * | 150 kgf/cm² |
| Amount of Aqueous Solution of Sodium Hydrogen Carbonate Ejected | 16 litter/m² |
| Ejection Time | 60 second/m² |
| Nozzle | Single Lance |

Note:
*Pressure of ejection from nozzle.

These weeds were killed with the leaves of *Coix lacryma-jobi* and Japanese nutmeg turned yellow and the leaves of *Pueraria lobata* and *Solidago serotina* turned black the next day of treatment in an area where the above treatment was carried out.

EXAMPLE 10

Weeds mainly consisting of *Pueraria lobata, Cayratia japonica*, Japanese nutmeg and *Coix lacryma-jobi* having an average height of about 60 cm on a roadside in Yokohama-city, Kanagawa-prefecture, Japan were subjected to a field weeding test, by a normal-temperature, high-pressure water blasting method, in which sodium hydrogen carbonate powder was added to high-pressure water in a blasting nozzle, under the conditions shown in Table 11 using a blasting apparatus ("Jetman FCPS-1030", available from Zaoh Sangyo K. K.) in July.

TABLE 11

Conditions of Normal-Temperature, High-Pressure Water Blasting Method

| | |
|---|---|
| Ejection Pressure of Water (gauge pressure)[1] | 150 kgf/cm² |
| Amount of Water Ejected | 16 liter/m² |
| Sodium Hydrogen Carbonate Powder | Flow Formula XL[2] |
| Amount of Sodium Hydrogen Carbonate Powder Added | 200 g/L |
| Ejection Time | 60 second/m² |
| Nozzle | Single Lance |

Note:
[1] Pressure of ejection from nozzle.
[2] Having a particle size of 300 μm, available from Church & Dwight Co., Inc.

These weeds were killed with the leaves of *Coix lacryma-jobi* and Japanese nutmeg turned yellow and the leaves of *Pueraria lobata* and *Cayratia japonica* turned black the next day of treatment in an area where the above treatment was carried out.

EXAMPLE 11

Weeds mainly consisting of *Pueraria lobata, Cayratia japonica* and *Solidago serotina* having an average height of about 60 cm on a roadside in Yokohama-city, Kanagawa-prefecture, Japan were subjected to a field weeding test by a steam blasting method under the conditions shown in Table 12 using a blasting apparatus ("Jetman FCPS-1030" with a hot box, available from Zaoh Sangyo K. K.) in July.

TABLE 12

Conditions of Steam Blasting Method

| | |
|---|---|
| Aqueous Solution of Sodium Hydrogen Carbonate | 80° C., 140 g/L |
| Ejection Pressure (gauge pressure)[1] | 150 kgf/cm² |
| Amount of Aqueous Solution of Sodium Hydrogen Carbonate Ejected | 16 litter/m² |
| Ejection Time | 60 second/m² |
| Nozzle | Double Lance |

Note:
[1] Pressure of ejection from nozzle.

All of these weeds were killed with their leaves turned black the next day of treatment in an area where the above treatment was carried out.

EXAMPLE 12

Weeds mainly consisting of *Pueraria lobata, Cayratia japonica* and *Solidago serotina* having an average height of about 60 cm on a roadside in Yokohama-city, Kanagawa-prefecture, Japan were subjected to a field weeding test by a steam blasting method under the conditions shown in Table 13 using a blasting apparatus ("Jetman FCPS-1030" with a hot box, available from Zaoh Sangyo K. K.) in July.

TABLE 13

Conditions of Steam Blasting Method

| | |
|---|---|
| Temperature of Heated Water | 80° C. |
| Ejection Pressure of Heated Water (gauge pressure)[1] | 150 kgf/cm² |
| Amount of Heated Water Ejected | 16 litter/m² |
| Sodium Hydrogen Carbonate Powder | Flow Formula XL[2] |
| Amount of Sodium Hydrogen Carbonate Powder Added | 200 g/L |
| Ejection Time | 60 second/m² |
| Nozzle | Double Lance |

Note:
[1] Pressure of ejection from nozzle.
[2] Having a particle size of 300 μm, available from Church & Dwight Co., Inc.

All of these weeds were killed with their leaves turned black the next day of treatment in an area where the above treatment was carried out.

As described above in detail, by spraying sodium hydrogen carbonate powder and/or an aqueous dispersion or solution of sodium hydrogen carbonate to weeds according to the weeding method of the present invention, the weeds can be killed, and those of the next generation can be dwarfed. Particularly by using a blast-weeding method, it is possible to carry out the weeding quickly and strongly. In addition, because sodium hydrogen carbonate is inexpensive and soluble in water with only extremely little influence on the environment, the weeding method of the present invention is suitable for treating weeds on riverbanks, roads, railroads, airports, parks, farms, golf courses, etc. Because the weeding method of the present invention can substantially remove only higher weeds than a proper level, it is particularly suitable for the weeding operation in airports, etc., in which low weeds should be left intact.

What is claimed is:

1. A weeding method comprising spraying a composition consisting essentially of an herbicidally-effective amount of sodium hydrogen carbonate powder and/or an aqueous dispersion or solution of sodium hydrogen carbonate onto weeds, whereby said sodium hydrogen carbonate acts on said weeds.

2. The weeding method according to claim 1, wherein said sodium hydrogen carbonate powder and/or said aqueous dispersion or solution of sodium hydrogen carbonate is sprayed to weeds by gravity drop or a low-pressure spraying apparatus.

3. The weeding method according to claim 2, wherein said aqueous dispersion or solution of sodium hydrogen carbonate has a concentration of 5–15 weight %.

4. The weeding method according to claim 2, wherein said sodium hydrogen carbonate powder has an average particle size of 10–500 μm.

5. The weeding method according to claim 1, wherein the amount of said sodium hydrogen carbonate powder and/or said aqueous dispersion or solution of sodium hydrogen carbonate is 0.00001–3.5 kg/m² by dry weight per a unit area of a field having weeds.

6. The weeding method according to claim 1, wherein said sodium carbonate powder and/or said aqueous dispersion or solution of sodium hydrogen carbonate is sprayed to weeds, after cutting high weeds.

7. A weeding method comprising spraying sodium hydrogen carbonate powder and/or aqueous dispersion or solution of sodium hydrogen carbonate as the active ingredient to weeds, wherein said sodium hydrogen carbonate powder and/or an aqueous dispersion or solution of sodium hydrogen carbonate is blasted onto said weeds at a pressure of at least 1 kgf/cm².

8. The weeding method according to claim 7, wherein said sodium hydrogen carbonate powder is blasted to weeds together with compressed air at an ejection pressure (gauge pressure) of 1–10 kgf/cm², using a high-pressure dry-blasting apparatus.

9. The weeding method according to claim 8, wherein said sodium hydrogen carbonate powder has an average particle size of 10–500 μm.

10. The weeding method according to claim 7, wherein an aqueous dispersion or solution of sodium hydrogen carbonate is prepared in advance, and blasted to weeds at an ejection pressure (gauge pressure) of 100–2,500 kgf/cm² through a blasting nozzle of a high-pressure wet-blasting apparatus.

11. The weeding method according to claim 10, wherein said aqueous dispersion or solution of sodium hydrogen carbonate has a concentration 5–15 weight %.

12. The weeding method according to claim 7, comprising using a high-pressure wet-blasting apparatus equipped with a high-pressure pump and a blasting nozzle;

conveying water by said high-pressure pump to said blasting nozzle; adding sodium hydrogen carbonate powder to the incoming high-pressure water at said blasting nozzle; and blasting the resultant mixture to weeds at an ejection pressure (gauge pressure) of 100–2,500 kgf/cm².

13. The weeding method according to claim 12, wherein 100–500 g of said sodium hydrogen carbonate powder is added per one litter of water.

14. The weeding method according to claim 12 or 13, wherein said sodium hydrogen carbonate powder has an average particle size of 200 μm or more.

15. The weeding method according to claim 7, wherein an aqueous dispersion or solution of sodium hydrogen carbonate heated at 50–150° C. is blasted to weeds at an ejection pressure (gauge pressure) of 50–500 kgf/cm² through a blasting nozzle of high-pressure wet-blasting apparatus.

16. The weeding method according to claim 15, wherein said aqueous dispersion or solution of sodium hydrogen carbonate has a concentration of 50–150 g/L.

17. (amended) The weeding method according to claim 7, comprising using a high-pressure wet-blasting apparatus equipped with a high-pressure pump and a blasting nozzle;

conveying heated water at 50–150° C. to said blasting nozzle by said high-pressure pump;

adding said sodium hydrogen carbonate powder to the incoming high-pressure, heated water at said blasting nozzle;

and blasting the resultant mixture to weeds at an ejection pressure (gauge pressure) of 50–500 kgf/cm².

18. The weeding method according to claim 17, wherein 100–500 g of said sodium hydrogen carbonate powder is added per one litter of said heated water.

19. The weeding method according to claim 11 or 12, wherein said sodium hydrogen carbonate powder has an average particle size of 200 μm or more.

* * * * *